US008926677B2

(12) United States Patent
Tomasello et al.

(10) Patent No.: US 8,926,677 B2
(45) Date of Patent: Jan. 6, 2015

(54) INTERSTITIAL ENERGY TREATMENT PROBE HOLDERS

(71) Applicant: Novian Health, Inc., Chicago, IL (US)

(72) Inventors: Anthony J. Tomasello, Sewickley Heights, PA (US); William Graveman, Tonganoxie, KS (US); Kambiz Dowlatshahi, Chicago, IL (US); Henry R. Appelbaum, Chicago, IL (US)

(73) Assignee: Novian Health, Inc., Chicago, IL (US)

( * ) Notice: Subject to any disclaimer, the term of this patent is extended or adjusted under 35 U.S.C. 154(b) by 0 days.

(21) Appl. No.: 13/967,703

(22) Filed: Aug. 15, 2013

(65) Prior Publication Data

US 2013/0331828 A1 Dec. 12, 2013

Related U.S. Application Data

(63) Continuation of application No. 13/326,051, filed on Dec. 14, 2011, now Pat. No. 8,518,095, which is a continuation of application No. 11/957,040, filed on Dec. 14, 2007, now Pat. No. 8,092,507.

(60) Provisional application No. 60/888,223, filed on Feb. 5, 2007.

(51) Int. Cl.
*A61N 5/06* (2006.01)
*A61B 18/20* (2006.01)
*A61B 18/24* (2006.01)
*A61B 19/00* (2006.01)
*A61B 17/00* (2006.01)

(52) U.S. Cl.
CPC ............... *A61B 18/20* (2013.01); *A61B 18/24* (2013.01); *A61N 5/0601* (2013.01); *A61B 19/201* (2013.01); *A61B 2017/00101* (2013.01); *A61B 2018/2005* (2013.01)
USPC .................... 607/89; 607/88; 607/96; 606/13

(58) Field of Classification Search
CPC ............. A61B 2018/0091; A61B 2018/00005; A61B 2018/00053; A61B 2018/00994; A61B 19/0256; A61B 19/26; A61B 19/20; A61B 19/22
USPC ....................... 607/88–93, 96; 606/1, 13, 130
See application file for complete search history.

(56) References Cited

U.S. PATENT DOCUMENTS

| 1,968,997 A | 8/1934 | Drucker |
| 2,189,989 A | 2/1940 | Lichtman |

(Continued)

FOREIGN PATENT DOCUMENTS

| DE | 2826383 | 12/1979 |
| JP | 2001148280 | 9/1989 |

(Continued)

OTHER PUBLICATIONS

Dowlatshahi, Kambiz, MD., et al. "Stereotactically Guided Laser Therapy of Occult Breast Tumors," published by Arch Surg in Nov. 2000.
Dowlatshahi, Kambiz, MD., "Laser Therapy of Small Breast Cancers." Presented at the Third Annual Meeting of the American Society of Breast Surgeons, Apr. 24-28, 2002. 152-166.
Dowlatshahi, Kambiz, MD., "Interstitial Laser Treatment of Small Breast Cancers," *Lasers in Medicine, Surgery, and Dentistry*. 2003. 677-689.

(Continued)

*Primary Examiner* — Ahmed Farah
(74) *Attorney, Agent, or Firm* — Neal, Gerber & Eisenberg LLP

(57) ABSTRACT

An interstitial laser energy treatment apparatus having co-acting movable probe holders which facilitate positioning of a laser probe and thermal probe in different positions relative to a tissue mass such as the tumor to be treated and relative to each other to facilitate treating tissue masses based on the exact position, size and shape of the tissue mass.

24 Claims, 14 Drawing Sheets

(56) References Cited

U.S. PATENT DOCUMENTS

| | | | |
|---|---|---|---|
| 3,753,657 A | 8/1973 | Downing et al. |
| 4,222,375 A | 9/1980 | Martinez |
| 4,402,311 A | 9/1983 | Hattori |
| 4,407,282 A | 10/1983 | Swartz |
| 4,559,942 A | 12/1985 | Eisenberg |
| 4,616,656 A | 10/1986 | Nicholson et al. |
| 4,662,368 A | 5/1987 | Hussein et al. |
| 4,665,927 A | 5/1987 | Daily |
| 4,681,122 A | 7/1987 | Winters et al. |
| 4,744,627 A | 5/1988 | Chande et al. |
| 4,773,413 A | 9/1988 | Hussein et al. |
| 4,774,948 A | 10/1988 | Markham |
| 4,776,334 A | 10/1988 | Prionas |
| 4,819,630 A | 4/1989 | Dehart |
| 4,880,122 A | 11/1989 | Martindell |
| 4,883,062 A | 11/1989 | Nicholson |
| 4,890,898 A | 1/1990 | Bentley et al. |
| 4,920,978 A | 5/1990 | Colvin |
| 4,931,059 A | 6/1990 | Markham |
| 4,932,934 A | 6/1990 | Dougherty |
| 4,946,440 A | 8/1990 | Hall |
| 4,950,267 A | 8/1990 | Ishihara et al. |
| 4,952,146 A | 8/1990 | Doty |
| 4,957,481 A | 9/1990 | Gatenby |
| 4,959,063 A | 9/1990 | Kojima |
| 4,961,422 A | 10/1990 | Marchosky et al. |
| 4,967,765 A | 11/1990 | Turner et al. |
| 5,019,075 A | 5/1991 | Spears et al. |
| 5,050,597 A | 9/1991 | Daikuzono |
| 5,059,197 A | 10/1991 | Urie et al. |
| 5,061,265 A | 10/1991 | Abela et al. |
| 5,078,142 A | 1/1992 | Siczek et al. |
| 5,125,925 A | 6/1992 | Lundahl |
| 5,127,916 A | 7/1992 | Spencer et al. |
| 5,129,896 A | 7/1992 | Hasson |
| 5,150,704 A | 9/1992 | Tatebayashi et al. |
| 5,158,084 A | 10/1992 | Ghiatus |
| 5,169,396 A | 12/1992 | Dowlatshahi et al. |
| 5,178,148 A | 1/1993 | Lacoste et al. |
| 5,178,164 A | 1/1993 | Allen |
| 5,195,526 A | 3/1993 | Michelson |
| 5,222,953 A | 6/1993 | Dowlatshahi |
| 5,234,426 A | 8/1993 | Rank et al. |
| 5,240,011 A | 8/1993 | Assa |
| 5,242,437 A | 9/1993 | Everett et al. |
| 5,312,392 A | 5/1994 | Hofstetter et al. |
| 5,323,779 A | 6/1994 | Hardy et al. |
| 5,330,517 A | 7/1994 | Mordon et al. |
| 5,386,447 A | 1/1995 | Siczek |
| 5,396,897 A | 3/1995 | Jain et al. |
| 5,398,899 A | 3/1995 | Austin et al. |
| RE34,936 E | 5/1995 | Campbell et al. |
| 5,415,169 A | 5/1995 | Siczek et al. |
| 5,460,066 A | 10/1995 | Dennstedt |
| 5,505,203 A | 4/1996 | Deitrich et al. |
| 5,520,182 A | 5/1996 | Leighton et al. |
| 5,569,240 A | 10/1996 | Dowlatshahi et al. |
| 5,615,430 A | 4/1997 | Nambu et al. |
| 5,620,479 A | 4/1997 | Diederich |
| 5,636,255 A | 6/1997 | Ellis |
| 5,673,696 A * | 10/1997 | Bidwell et al. ............... 600/437 |
| 5,735,264 A | 4/1998 | Siczek et al. |
| 5,813,985 A | 9/1998 | Carroll |
| 5,853,366 A | 12/1998 | Dowlatshahi |
| 5,954,711 A | 9/1999 | Ozaki et al. |
| 5,983,424 A | 11/1999 | Naslund |
| 6,023,637 A | 2/2000 | Liu et al. |
| 6,058,322 A | 5/2000 | Nishikawa et al. |
| 6,094,760 A | 8/2000 | Nonaka et al. |
| 6,241,725 B1 | 6/2001 | Cosman |
| 6,341,893 B1 | 1/2002 | Matsumoto et al. |
| 6,451,015 B1 | 9/2002 | Rittman et al. |
| 6,456,684 B1 | 9/2002 | Mun et al. |
| 6,500,343 B2 | 12/2002 | Siddiqi |
| 6,542,767 B1 | 4/2003 | McNichols et al. |
| 6,551,302 B1 | 4/2003 | Rosinko et al. |
| 6,562,028 B2 | 5/2003 | Nield et al. |
| 6,569,176 B2 | 5/2003 | Jesseph |
| 6,603,988 B2 | 8/2003 | Dowlatshahi |
| 6,671,535 B1 | 12/2003 | McNichols et al. |
| 6,701,175 B2 | 3/2004 | Dowlatshahi |
| 6,755,849 B1 | 6/2004 | Gowda et al. |
| 6,865,412 B2 | 3/2005 | Dowlatshahi |
| 6,928,672 B2 | 8/2005 | Pastyr et al. |
| 7,041,109 B2 | 5/2006 | Dowlatshahi |
| 7,074,233 B1 | 7/2006 | Gowda et al. |
| 7,171,253 B2 | 1/2007 | Dowlatshahi |
| 7,270,656 B2 | 9/2007 | Gowda et al. |
| 7,274,847 B2 | 9/2007 | Gowda et al. |
| 8,092,507 B2 * | 1/2012 | Tomasello et al. ............... 607/89 |
| 8,518,095 B2 * | 8/2013 | Tomasello et al. ............... 607/89 |
| 2002/0026127 A1 | 2/2002 | Balbierz et al. |
| 2003/0023236 A1 | 1/2003 | Gowda et al. |
| 2003/0035868 A1 | 2/2003 | Coulter et al. |
| 2003/0060813 A1 | 3/2003 | Loeb |
| 2004/0215101 A1 | 10/2004 | Rioux et al. |
| 2005/0113641 A1 | 5/2005 | Bala |
| 2005/0165287 A1 | 7/2005 | Westcott, III |
| 2005/0169596 A1 | 8/2005 | Hamasaki et al. |
| 2006/0095096 A1 | 5/2006 | DeBenedictis et al. |
| 2006/0104593 A1 | 5/2006 | Gowda et al. |
| 2006/0155298 A1 | 7/2006 | Mueller et al. |
| 2006/0217693 A1 | 9/2006 | Gowda et al. |
| 2006/0241727 A1 | 10/2006 | Dowlatshahi |
| 2007/0100229 A1 | 5/2007 | Dowlatshahi |
| 2007/0119738 A1 | 5/2007 | Clegg et al. |
| 2007/0219544 A1 | 9/2007 | Gowda et al. |
| 2007/0290703 A1 | 12/2007 | Hollman |
| 2008/0015560 A1 | 1/2008 | Gowda et al. |
| 2008/0114340 A1 | 5/2008 | Fox et al. |

FOREIGN PATENT DOCUMENTS

| | | |
|---|---|---|
| JP | 2000237205 | 5/2000 |
| WO | WO8704611 | 8/1987 |
| WO | WO0013603 | 3/2000 |
| WO | WO0059394 | 10/2000 |
| WO | WO03011160 | 2/2003 |
| WO | WO2005046753 | 5/2005 |
| WO | WO2006055554 | 5/2006 |

OTHER PUBLICATIONS

Dowlatshahi, Kambiz, MD., et al. "Laser Therapy of Breast Cancer with 3-Year Follow-up." *The Breast Journal*, vol. 10, No. 3, 2004. 240-243.

Dowlatshahi, Kambiz, MD., "Shift in the Surgical Treatment of Non-Palpable Breast Cancer: Tactile to Visual." Rush University Medical Center. Breast Cancer Online <http://www.bco.org>, Oct. 9, 2005, 1-10.

International Preliminary Report on Patentability for PCT/US2008/052911 dated Aug. 11, 2009.

Kelsey. "Revolutionizing Breast Treatment with Interstitial Laser Therapy." May 2003. 1-22.

Kelsey. "Revolutionizing Breast Treatment with Interstitial Laser Therapy." Feb. 2005. 1-18.

Mammography Biopsy Chair Brochure written by Hausted, published in 1993.

Mammomat 3000 Nova Brochure written by Siemens, published prior to 2000.

Multifunctional Mammography—High Patient Throughput, Favorable Economics Brochure written by Siemens, published in 1999.

Sonoline Antares—A New Dimension in Ultrasound Brochure written by Siemens, published prior to 2002.

Written Opinion of the International Searching Authority for International Application No. PCT/US08/50358 dated Nov. 7, 2008.

* cited by examiner

350A

350B

350C

INTERSTITIAL ENERGY TREATMENT PROBE HOLDERS

PRIORITY CLAIM

This application is a continuation of, claims priority to and the benefit of U.S. patent application Ser. No. 13/326,051, filed on Dec. 14, 2011, which is a continuation of, claims priority to and the benefit of U.S. patent application Ser. No. 11/957,040, filed Dec. 14, 2007, now U.S. Pat. No. 8,092,507, which is a non-provisional application of, claims priority to and the benefit of U.S. Provisional Patent Application No. 60/888,223, filed Feb. 5, 2007, each of which are incorporated herein by reference in their entirety.

DESCRIPTION

The present disclosure relates in general to apparatus and methods for delivering ablative laser energy to tissue such as tumors, and in particular to apparatus and methods for positioning a laser probe to deliver ablative laser energy to tissue and for positioning a thermal probe relative to the laser probe to monitor the temperature of surrounding tissue.

BACKGROUND

Percutaneous in situ or on-site laser therapy treatment of tissue such as tumors and in particular malignant breast tumors can be more readily performed today because tissue abnormalities such as tumors are being detected at earlier stages. Tissue abnormalities such as breast cancer and other cancers or tumors detected in early development can be effectively treated or destroyed using an ablative agent such as laser energy without conventional surgery.

Interstitial laser energy treatments of tissue (such as tumors) including malignant tumors (such as breast, liver, brain, and neck tumors), have been in development for more than a decade. For example, U.S. Pat. No. 5,169,396, U.S. Pat. No. 5,222,953, U.S. Pat. No. 5,569,240, U.S. Pat. No. 5,853,366, U.S. Pat. No. 6,603,988, U.S. Pat. No. 6,701,175, U.S. Pat. No. 6,865,412, U.S. Pat. No. 7,041,109, and U.S. Pat. No. 7,171,253 disclose various apparatus and methods for conducting interstitial laser energy treatments of tissue (such as tumors). Certain of these patents disclose a laser probe and a thermal probe for conducting the interstitial laser energy treatment and related temperature measurement. Certain of these patents also disclose a probe holder configured to hold the laser probe and the thermal probe. However, such probe holders are very limited in the relative positions and fixed geometries in which they can hold the laser probe and the thermal probe for conducting interstitial laser energy treatment. Certain of these patents disclose a probe holder configured to hold the thermal probe at a single fixed distance from the laser probe and in a single plane with the laser probe.

It has been determined that known probe holders do not fully facilitate interstitial laser energy treatment of: (a) body parts of different sizes and shapes (such as breasts) containing the tissue to be treated; (b) tissue to be treated (such as tumors) of different sizes and shapes; (c) different areas of the body containing the tissue to be treated; and (d) variations in the tissue surrounding the area to be treated. These known probe holders also do not enable operators to properly account for variations in the tissue surrounding the area to be ablated. Accordingly, there is a need for methods and apparatus for interstitial laser energy treatment having a probe holder apparatus which facilitates the above variations.

SUMMARY

One embodiment of the present disclosure provides an interstitial laser energy treatment apparatus having probe holder apparatus including co-acting independently movable probe holders which facilitate positioning of a laser probe in a suitable position relative to tissue (such as a tumor) to be treated and which facilitate positioning of a thermal probe in a plurality of different positions and geometries relative to the tissue to be treated and relative to the laser probe. The probe holders enable operators to consistently and reliably position the thermal probe at different, predetermined distances from laser probe and to position the thermal probe together with the laser probe in multiple different planes throughout a known or predetermined geometry. The movable probe holders enable an operator to: (a) place the laser probe in the body of a patient in a desired position for treating the tissue based on the exact position, size, and shape of the tissue and the body part containing the tissue; and (b) place the thermal probe in the body of a patient in proximity with and substantially parallel to the laser probe based on the position of the laser probe, the exact position, size, and shape of the tissue to be treated, and the body part containing the tissue. This positioning enables the laser probe to facilitate delivery of laser energy to the tissue and the thermal probe to measure the tissue temperature at various locations in proximity of the tissue (such as the tumor) being treated during interstitial laser therapy. This positioning also enables the operator to account for variations in tissue surrounding the area to be ablated.

It is therefore an advantage of the present disclosure to provide an interstitial laser energy treatment apparatus having probe holder apparatus including one or more probe holders which facilitate positioning of a laser probe and a thermal probe in desired positions relative to the tissue to be treated and relative to each other for interstitial laser energy treatment.

DETAILED DESCRIPTION OF EXEMPLARY EMBODIMENTS

Figure 1:
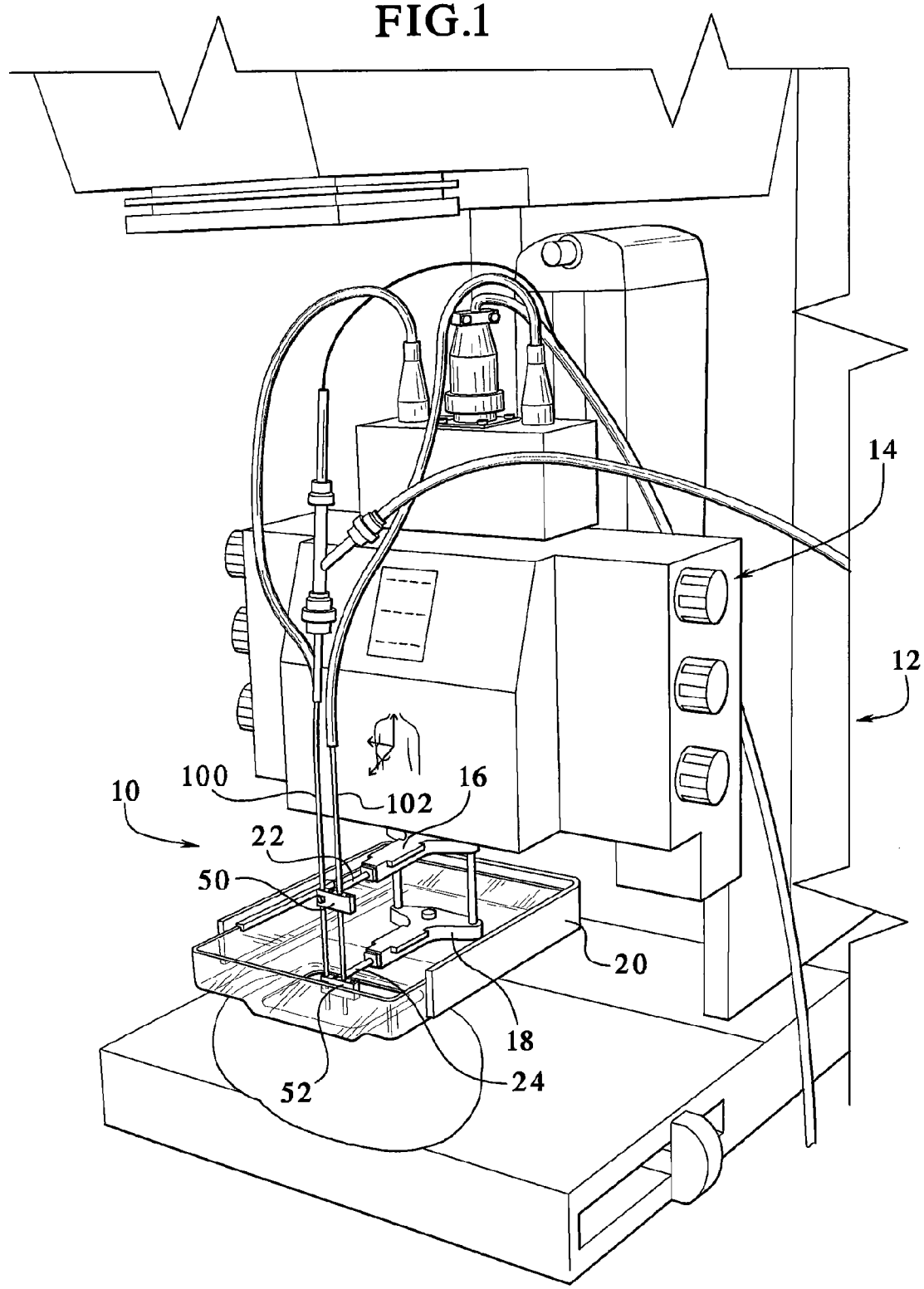
FIG. 1 is a fragmentary perspective view of one embodiment of the interstitial laser energy treatment apparatus disclosed herein, illustrating the laser probe holders respectively aligned in first positions for positioning the laser probe and thermal probe in a first plane relative to tissue.
Figure 2:
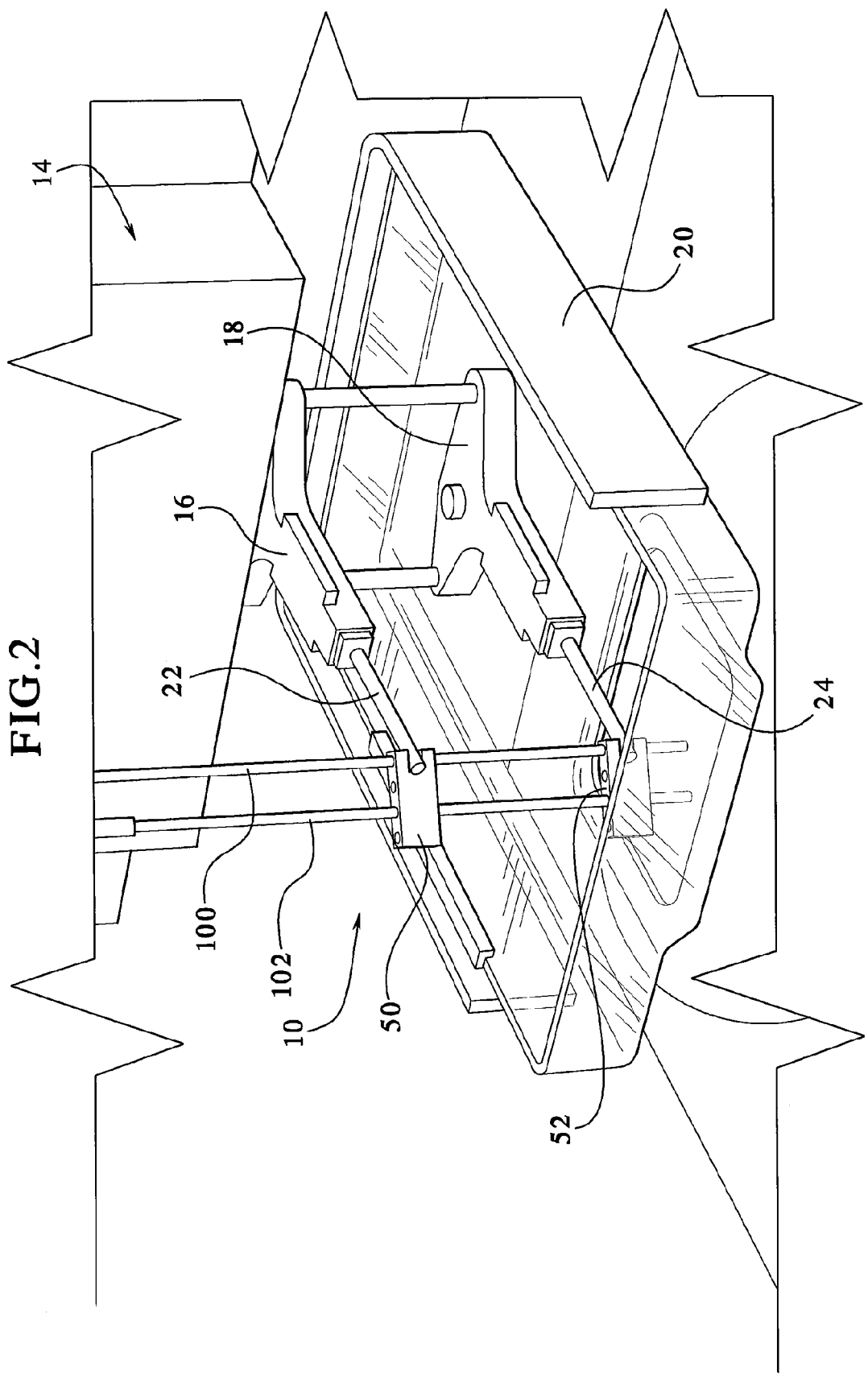
FIG. 2 is an enlarged fragmentary perspective view of the embodiment of the interstitial laser energy treatment apparatus of FIG. 1, showing the laser probe holders respectively aligned in different second positions (than those shown in FIG. 1) for positioning the laser probe and thermal probe in a different second plane relative to the tissue.
Figure 3:
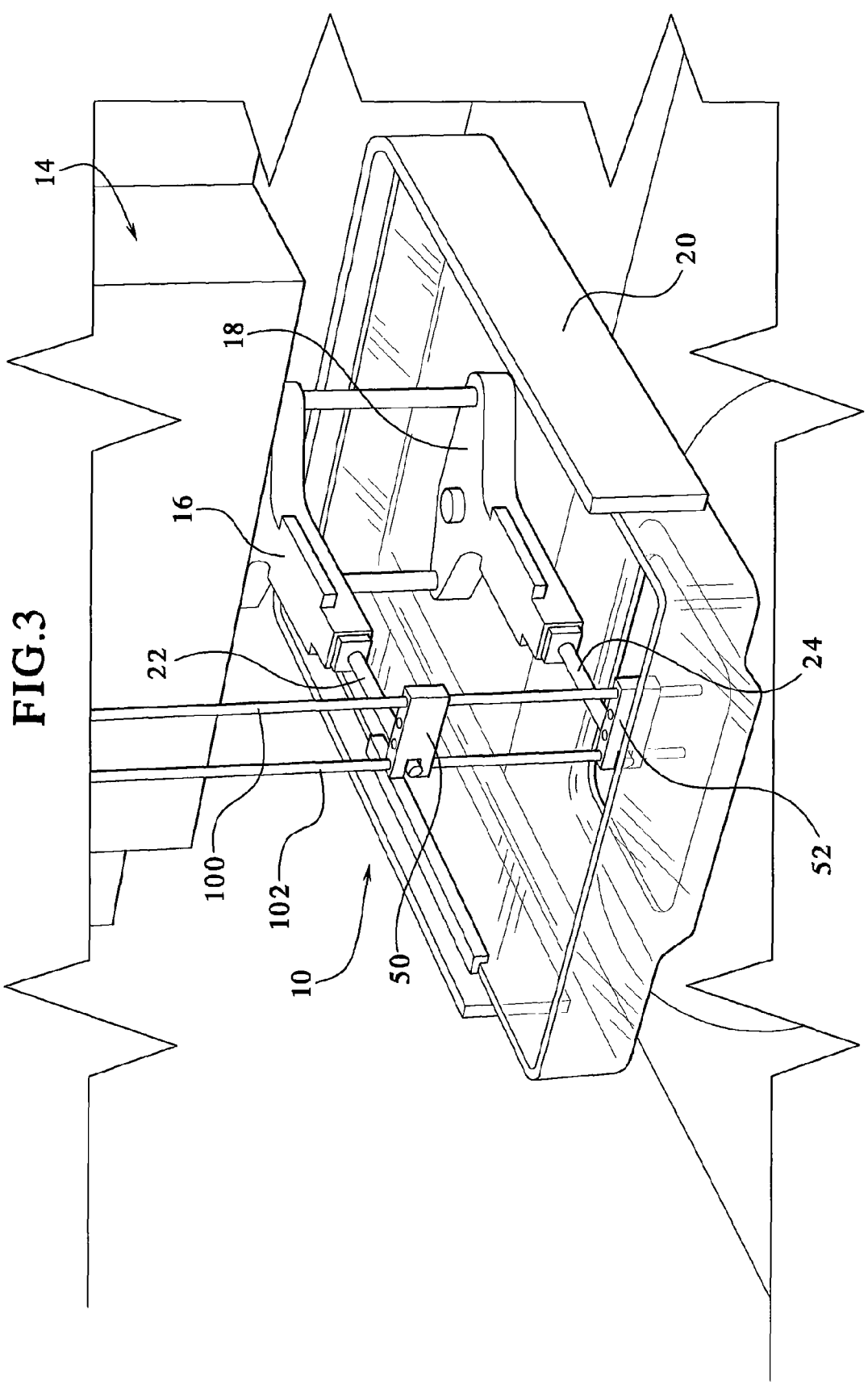
FIG. 3 is an enlarged fragmentary perspective view of the embodiment of the interstitial laser energy treatment apparatus of FIG. 1, showing the laser probe holders respectively aligned in the first positions (as in FIG. 1) and with the thermal probe at a further distance from the laser probe than in FIG. 1.

Referring now to the drawings, and particularly to FIGS. 1, 2, 3, 4, 5, and 6, one embodiment of the interstitial laser energy treatment apparatus 10 is shown attached to or mounted on an imaging device or unit such as a conventional rotatable or positionable digital mammography device or unit 12. The mammography unit 12 includes a suitable stereotactic device or unit 14. It should be appreciated that the imaging device or unit may be any suitable unit or device including but not limited to x-ray, ultrasound, or magnetic resource imaging devices. It should also be appreciated that the stereotactic device or unit may be any suitable device or unit. The illustrated stereotactic device 14 includes conventional aligned extendable upper (or first) and lower (or second) biopsy needle holders 16 and 18, respectively, suitably attached at the bottom of the stereotactic device 14. The illustrated stereotactic device 14 includes a compression plate 20 suitably attached at the bottom of the stereotactic device 14 below the upper and lower biopsy needle holders 16 and 18. For ease of illustration, FIGS. 1, 2 and 3, show a saline bag instead of a body part (such as a breast) containing the tissue which would be treated using the interstitial laser energy treatment apparatus.

The upper and lower biopsy needle holders 16 and 18 include outwardly extending aligned movable upper and lower needle holder arms 22 and 24, respectively, which are conventionally configured to removably hold and position a biopsy needle (not shown). The end sections of the arms 22 and 24 have vertically aligned vertically extending apertures through which the biopsy needle (not shown) is inserted for positioning and insertion into a body part (such as a breast) to perform a biopsy. These arms are employed in conjunction with the probe holders as described below to accurately and consistently position the laser probe and thermal probe of the interstitial laser therapy apparatus. It should be appreciated that the holders and arms can be configured in other suitable manners. As illustrated in FIGS. 1, 2 and 3, the upper and lower probe holders 50 and 52 of the interstitial laser energy treatment apparatus 10 are configured to be positioned at the end sections of the upper and lower needle holder arms 22 and 24 respectively to position a laser probe 100 and the thermal probe 102 for interstitial laser energy treatment. In certain embodiments disclosed herein, the probe holders 50 and 52 are not connected to facilitate independent positioning relative to the movable arms which for different patients may be positioned at different distances from each other.

Figure 4:
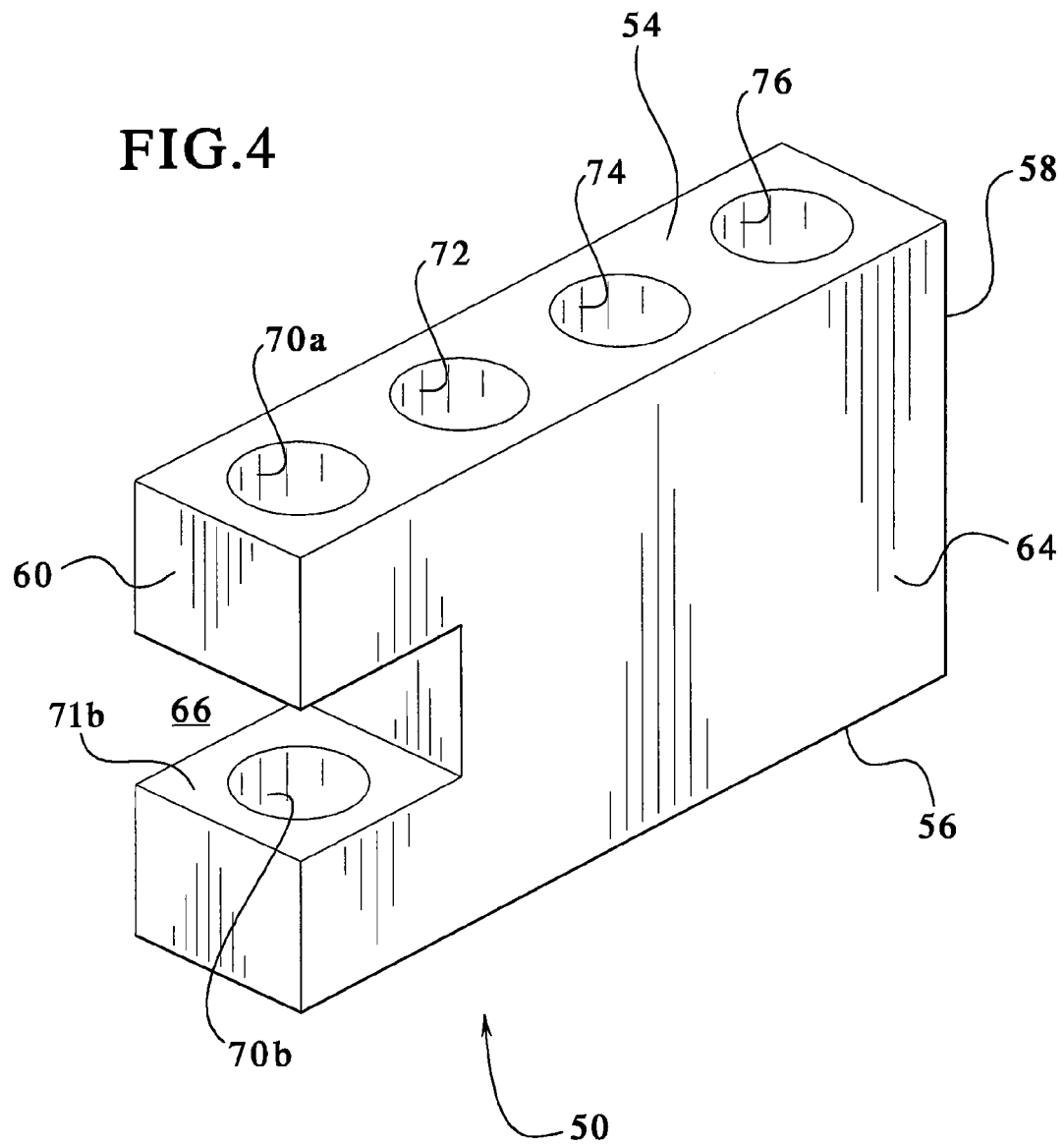
FIG. 4 is an enlarged perspective view of the embodiment of one of the laser probe holders of FIG. 1, shown removed from the interstitial laser energy treatment apparatus, illustrating a laser probe channel and the three spaced-apart thermal probe channels.
Figure 5:
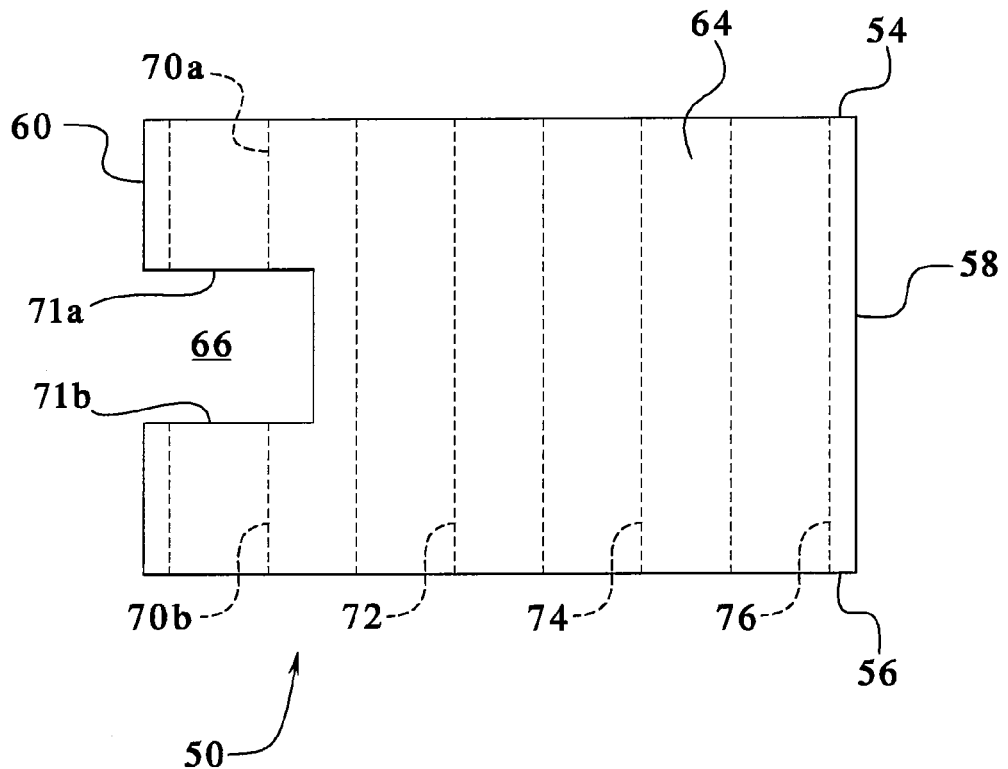
FIG. 5 is a side view of the embodiment of the laser probe holder of FIG. 4, shown removed from the interstitial laser energy treatment apparatus, illustrating in phantom the aligned laser probe channels and the three spaced-apart thermal probe channels.
Figure 6:
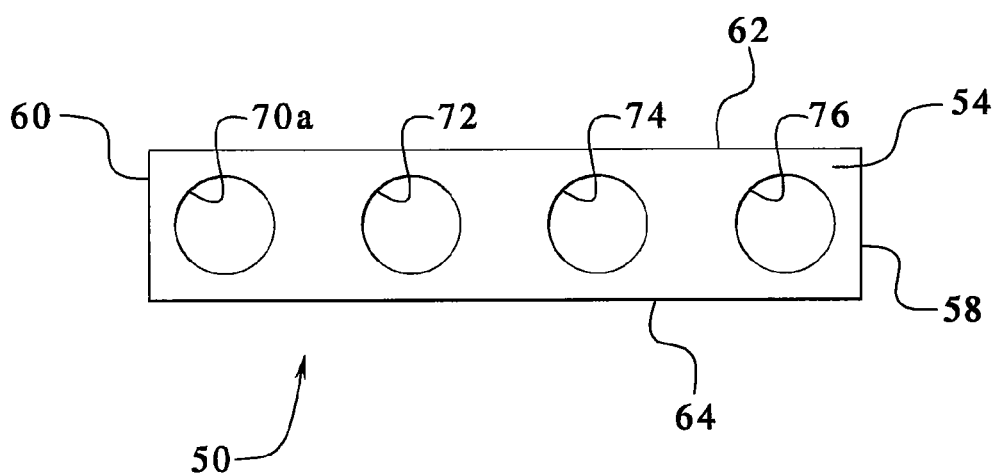
FIG. 6 is a top plan view of the embodiment of the laser probe holder of FIG. 4, shown removed from the interstitial laser energy treatment apparatus, illustrating the aligned laser probe channels and the three spaced-apart thermal probe channels.

More specifically, the probe holders 50 and 52 are preferably identical in shape, size and material. However, they may be varied in shape, size and material. FIGS. 4, 5 and 6 are used to illustrate both probe holders 50 and 52, but are discussed particularly with reference to probe holder 50. In one embodiment, the probe holder 50 generally includes a generally rectangular solid plastic body having a length, width, and depth. It should be appreciated that the probe holder may be formed in alternative shapes as further discussed below. The body of the probe holder 50 includes a top wall or surface 54, a bottom wall or surface 56, a front wall or surface 58, a rear wall or surface 60, and two side walls or surfaces 62 and 64. The rear or first portion or section of the body includes or defines a needle holder arm receiving area 66 sized and configured to receive the end section of the respective needle holder arm as illustrated. The rear or first portion or section of the body also defines or includes vertically aligned laser probe receiving channels 70a and 70b positioned in the body on opposite sides of the arm receiving area 66. Channel 70a extends from the top surface or wall 54 to a top wall 71a which defines the arm receiving area 66 and channel 70b extends from the bottom wall or surface 56 to a bottom wall 71b which defines the arm receiving area 66. The probe holder 50 also includes a front or second portion or section defining spaced-apart parallel or substantially parallel thermal probe receiving channels 72, 74, and 76 extending from the top wall or surface 54 to the bottom wall or surface 56.

In the embodiments illustrated herein, all of the laser probe and thermal probe channels are cylindrical; however, it should be appreciated that one or more of the channels may be formed in other suitable shapes and that different channels may be of different shapes. It should also be appreciated that the spacing between the channels may vary. It should further be appreciated that each of the size of the channels, shape of the channels, number of channels, and distance between the channels may vary depending on the type of procedure for which the channels are employed.

Referring again to FIGS. 1 and 2, the illustrated embodiment of the interstitual laser treatment apparatus 10 includes a laser probe 100 and a temperature or thermal probe 102 configured to be held in position by the upper probe holder 50 positioned at the end of the upper needle holder arm 22 and a lower probe holder 52 positioned at the end of the lower needle holder arm 24. The upper and lower probe holders are shown aligned in first positions in FIG. 1 and in different second positions in FIG. 2 to illustrate that the interstitial laser apparatus disclosed herein facilitates the thermal probe and laser probe being aligned in various different vertical planes in a geometry about the axis of the laser probe. It should be appreciated that the thermal probe may be aligned in one of a plurality of different planes with respect to the laser probe. In the illustrated embodiment, the different planes each extend in an arc or partial arc around the axis of rotation of the laser probe as further discussed below.

In operation, the laser probe 100 is removably inserted through the needle arm apertures (not shown) and the laser probe channels of the aligned probe holders, and the thermal probe 102 is removably inserted through one of the sets of the aligned corresponding thermal probe channels of the aligned probe holders 50 and 52. The thermal probe 102 is held in fixed position or distance relative to the laser probe 100 by the probe holders 50 and 52. The thermal probe 102 is also held such that it remains co-planar or substantially co-planar with the laser probe 100.

More specifically, to position the laser probe 100, the operator positions the upper probe holder 50 at the end of the upper needle holder arm 22 such that laser probe channels 70a and 70b (of the upper probe holder 50) are vertically aligned with the aperture of the vertically extending arm 22 (i.e., above and below the end of the arm 22). The operator then inserts the laser probe 100 through the laser probe channel 70a, then through the aperture of the arm 22, and then through the laser probe channel 70b. It should be appreciated that in this embodiment the probe holder 50 is maintained in position relative to the arm 22 by the laser probe 100 once inserted. At this point, the probe holder 50 is pivotally movable about the axis of the laser probe.

In this embodiment, the operator then positions the lower probe holder 52 at the end of the lower needle holder arm 24 such that laser probe channels 70a and 70b (of the lower probe holder 52) are vertically aligned with the aperture of the vertically extending arm 24 (i.e., above and below the end of the arm 24). The operator then pushes down on the laser probe to insert the laser probe 100 through the laser probe channel 70a (of the lower probe holder 52), then through the aperture of the arm 24, and then through the laser probe channel 70b (of the lower probe holder 52). It should be appreciated that in this embodiment the probe holder 52 is maintained in position relative to the arm 22 by the laser probe 100 once inserted. At this point, the probe holder 52 is pivotally movable about the axis of the laser probe.

It should thus be appreciated that when the laser probe 100 is inserted through both probe holders 50 and 52 and through the arms 22 and 24, the probe holders 50 and 52 are each configured to independently to pivot about an axis of rotation extending substantially along the length of the laser probe 100. This enables the operator to position the laser probe holders in any one of a plurality of the different sets of positions relative to the laser probe. The operator can position the probe holders to select the plane in which the laser probe and thermal probe will be aligned.

For example, FIG. 1 shows the probe holders 50 and 52 aligned in a set of first positions or first plane. FIG. 2 shows the probe holders 50 and 52 aligned in a set of second positions (which are different than the first set of positions) and thus in a second, different plane. The determination of which positions and which planes will be used is at least in part based on the size and shape of the tissue (such as the tumor) being treated and at least in part based on where such tissue is located.

To position the thermal probe 102, the operator selects one of the respective sets of thermal probe channels in the probe holders based on the operator's desired distance between the thermal probe 102 and the laser probe 100. This determination is also in part based on the size, shape of the tissue (such as the tumor) being treated and at least in part based on where such tissue is located. The operator inserts the thermal probe 102 through the selected set of thermal probe channels 72, 74, or 76 in the respective probe holders 50 and 52.

In one embodiment, the laser probe is inserted through the probe holders and arms, into the body part (such as the breast), and into the tissue to be treated (such as the tumor) before the thermal probe is inserted through the probe holders.

In another embodiment, the laser probe is inserted through the probe holders and arms but not into the body part (such as the breast) or into the tissue to be treated (such as the tumor) before the thermal probe is inserted through the probe holders. In this embodiment, after the laser probe and thermal probe are positioned, both are inserted into the patient. Also, in this embodiment, after inserting the laser probe, the operator may move the thermal probe to a different set of thermal probe channels before inserting the thermal probe into the patient.

It should be appreciated that the probe holders may be made from any suitable material such as a suitable plastic, a suitable metal, a suitable composite material, or any combination thereof. It is preferable that the probe holders are made of a material and are sized such that they do not interfere with the imaging device or unit. It should also be appreciated that the probe holder apparatus disclosed herein enable the probe holders to be easily moved or rotated out of the way of the imaging device.

Figure 7:
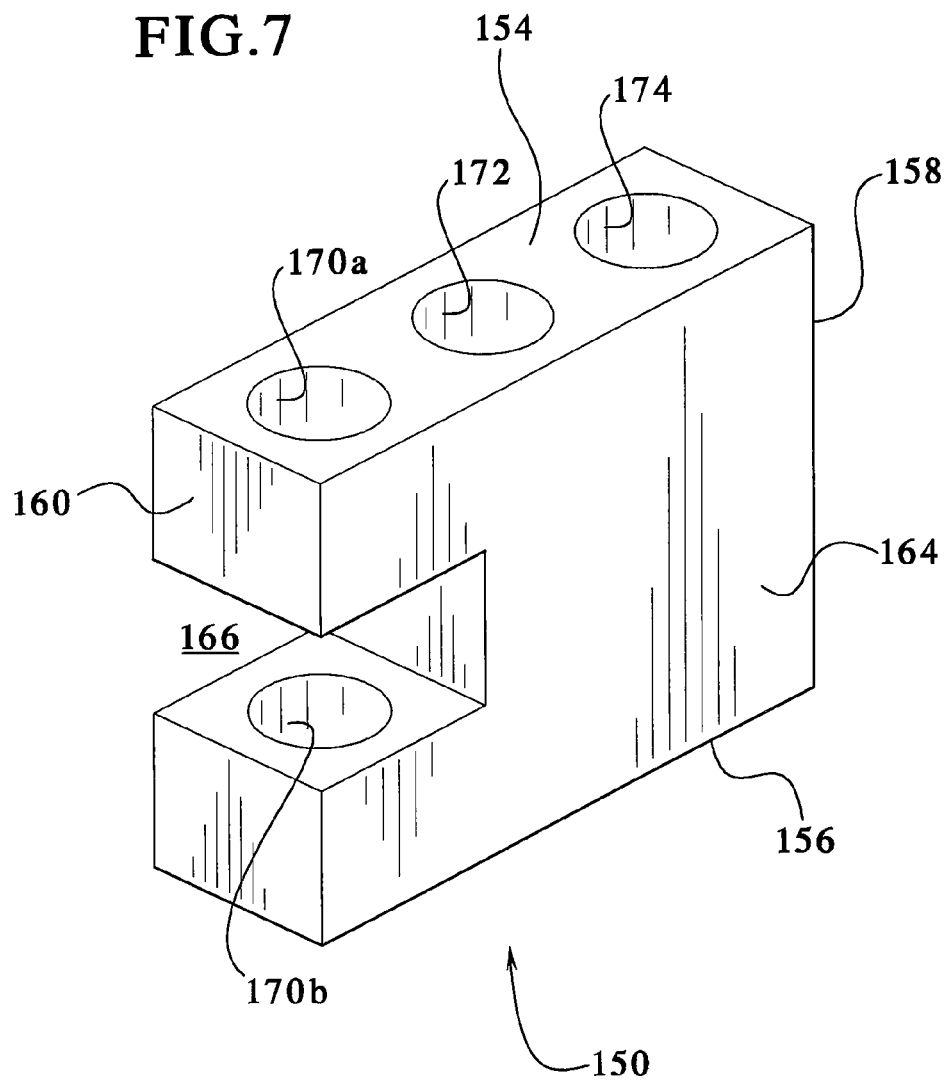
FIG. 7 is an enlarged perspective view of an alternative embodiment of the laser probe holder, shown removed from the interstitial laser energy treatment apparatus, illustrating the aligned laser probe channels and the two spaced-apart thermal probe channels.
Figure 8:
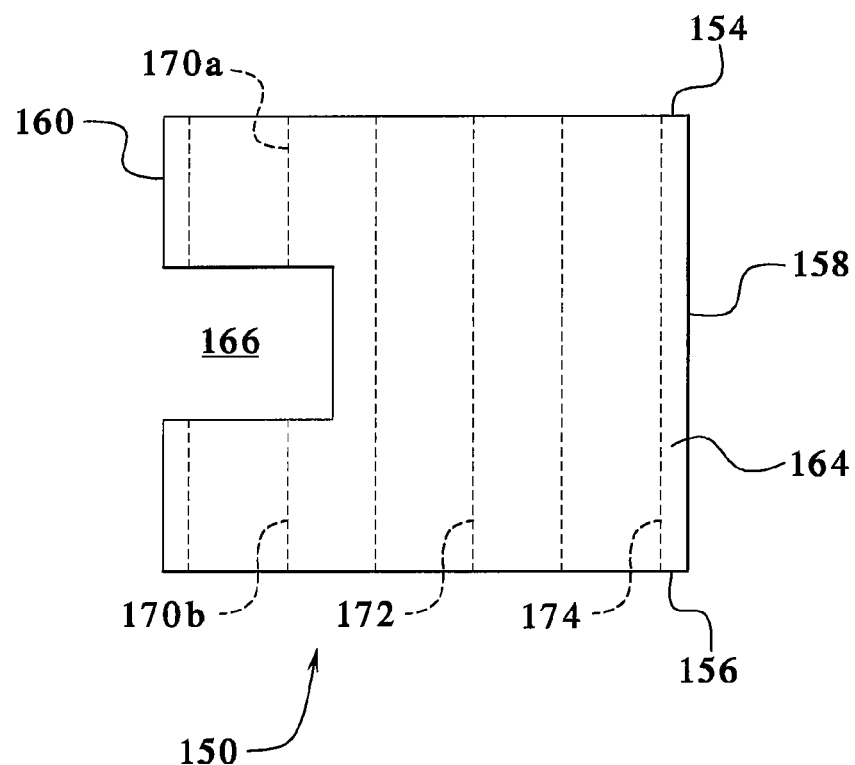
FIG. 8 is a side view of the embodiment of the laser probe holder of FIG. 7, shown removed from the interstitial laser energy treatment apparatus, illustrating in phantom the aligned laser probe channels and the two spaced-apart thermal probe channels.
Figure 9:
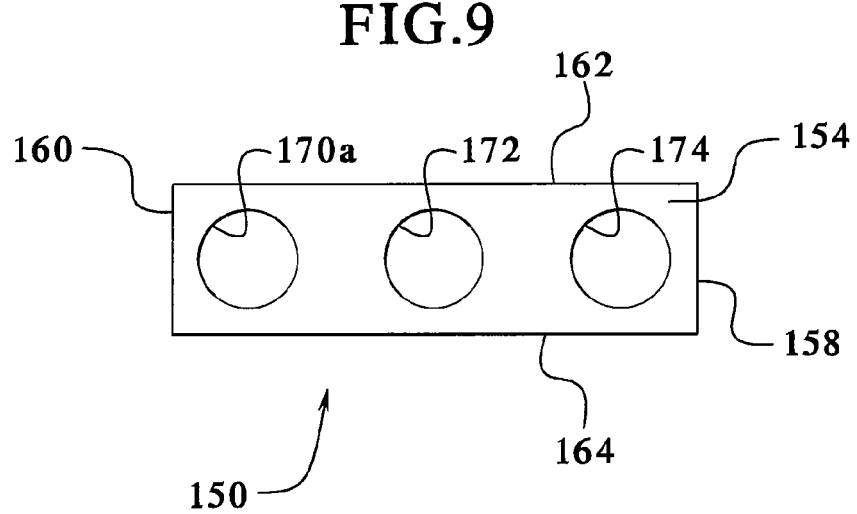
FIG. 9 is top plan view of the embodiment of the laser probe holder of FIG. 7, shown removed from the interstitial laser energy treatment apparatus, illustrating the aligned laser probe channels and the two spaced-apart thermal probe channels.

Turning now to FIGS. 7, 8, and 9, an alternative embodiment of the probe holder generally indicated by numeral 150 is illustrated. Probe holder 150 is similar to probe holder 50 as illustrated in FIGS. 4, 5, and 6, except that it has one fewer thermal probe receiving channel. It should thus be appreciated that the number of thermal probe receiving channels can vary in accordance with various embodiments of the present disclosure. More specifically, probe holder 150 includes a generally rectangular solid body having a top wall or surface 154, a bottom wall or surface 156, a front wall or surface 158, a rear wall or surface 160, and two side walls or surfaces 162 and 164. The rear potion of the body includes a needle holder arm receiving area 166 sized and configured to receive the end section of the respective needle holder arm. The probe holder body defines or includes vertically aligned laser probe receiving channels 170a and 170b and spaced-apart parallel thermal probe receiving channels 172 and 174.

Figure 10:
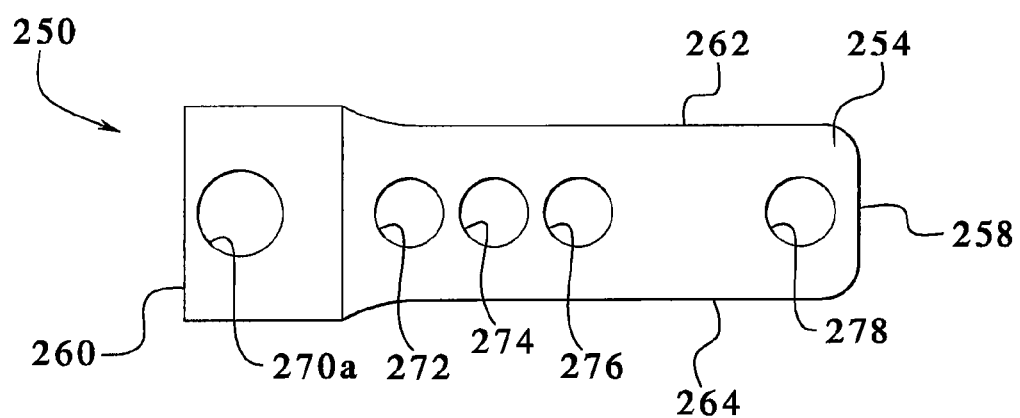
FIG. 10 is a top plan view of an alternative embodiment of the laser probe holder, shown removed from the interstitial laser energy treatment apparatus, illustrating the aligned laser probe channels and four spaced-apart thermal probe channels including three thermal probe channels adjacent to the laser probe channels and a fourth thermal probe channel spaced further apart from the three thermal channels.
Figure 11:
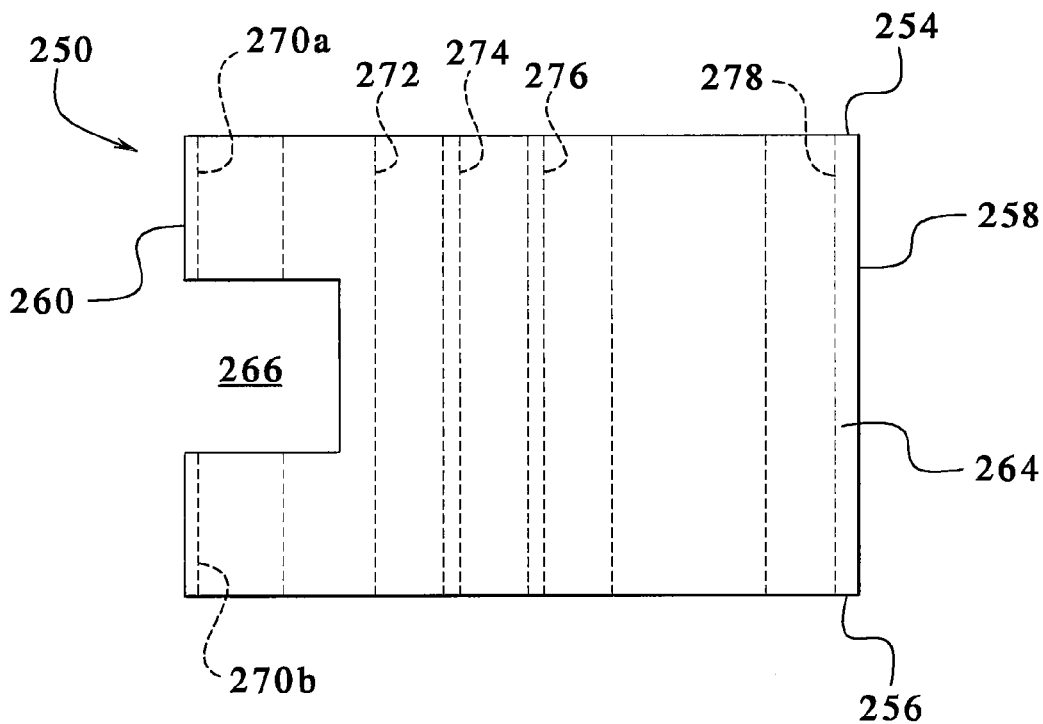
FIG. 11 is a side view of the embodiment of the laser probe holder of FIG. 10, shown removed from the interstitial laser energy treatment apparatus, illustrating in phantom the aligned laser probe channel and the four spaced-apart thermal probe channels.

It should be appreciated that the shape of the body of the probe holder may also vary. FIGS. 10 and 11 illustrate an alternative embodiment of the probe holder generally indicated by numeral 250 in which the rear section (having the laser probe channels) is wider than the front section (having the thermal probe channels). The probe holder 250 also illustrates one extra thermal probe channel than illustrated in FIGS. 4, 5, and 6, and that the thermal probe channels may be spaced in different patterns and that they may be spaced-apart at different distances. More specifically, the probe holder 250 includes a top wall or surface 254, a bottom wall or surface 256, a front wall or surface 258, a rear wall or surface 260, and two side walls or surfaces 262 and 264. The rear or first portion or section defines a needle holder arm receiving area 266. The rear or first portion or section also defines or includes vertically aligned laser probe receiving channels 270a and 270b. The probe holder 250 also includes spaced-apart parallel or substantially parallel thermal probe receiving channels 272, 274, 276, and 278.

Figure 12A:
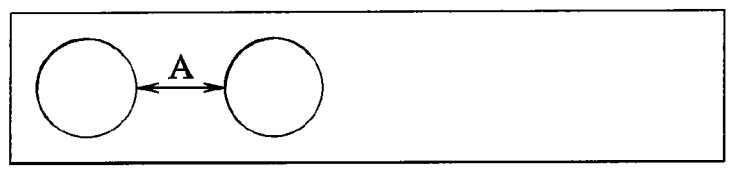
FIGS. 12A, 12B, and 12C are top plan views of a set of probe holders of a further alternative embodiment, each probe holder having one thermal probe channel.
Figure 12B:
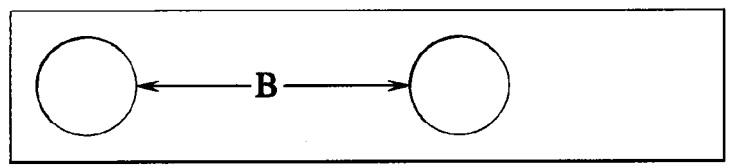
Figure 12C:
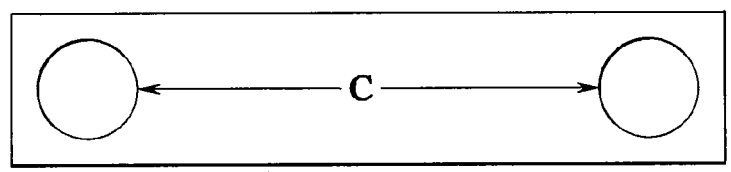

In another embodiment as illustrated in FIGS. 12A, 12B, and 12C, the probe holders are provided as a set of probe holders such as probe holders 350A, 350B, and 350C. The respective distances A, B, and C between the respective laser probe channels and the thermal probe channels differ for each probe holder 350A, 350B, and 350C. In this embodiment, the set of probe holders includes two probe holders 350A, two probe holders 350B, and two probe holders 350C. In this embodiment, the operator selects and uses the desired pair of probe holders 350A, 350B, or 350C, depending on the desired distance between the laser probe and the thermal probe.

Figure 13:
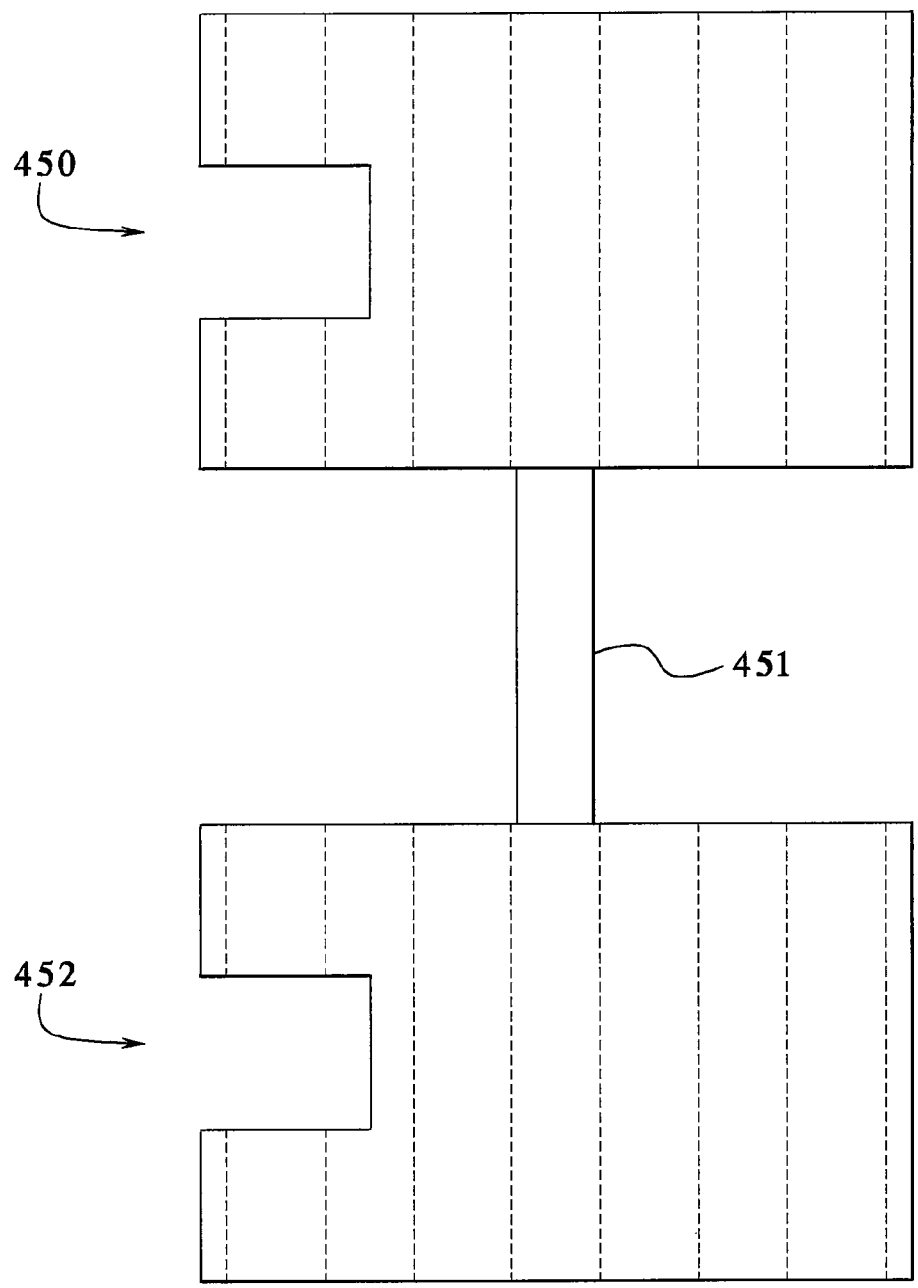
FIG. 13 is a side view of two connected probe holders of a further alternative embodiment.

In a further alternative embodiment as illustrated in FIG. 13, the individual probe holders 450 and 452 are suitably connect by at least one connection member or bar 451. The connection member or bar 451 holds the probe holders 450 and 452 together. This embodiment enables the operator to place or position both probe holders 450 and 452 together on the biopsy needle holder arms. In one such embodiment, the connection member or bar 451 is suitably removable. This removable functionality may be provided in any suitable manner. It should be appreciated that the connection member will be formed and positioned so as not to interfere with the probes before, during, or after positioning the probe holder.

Figure 14:
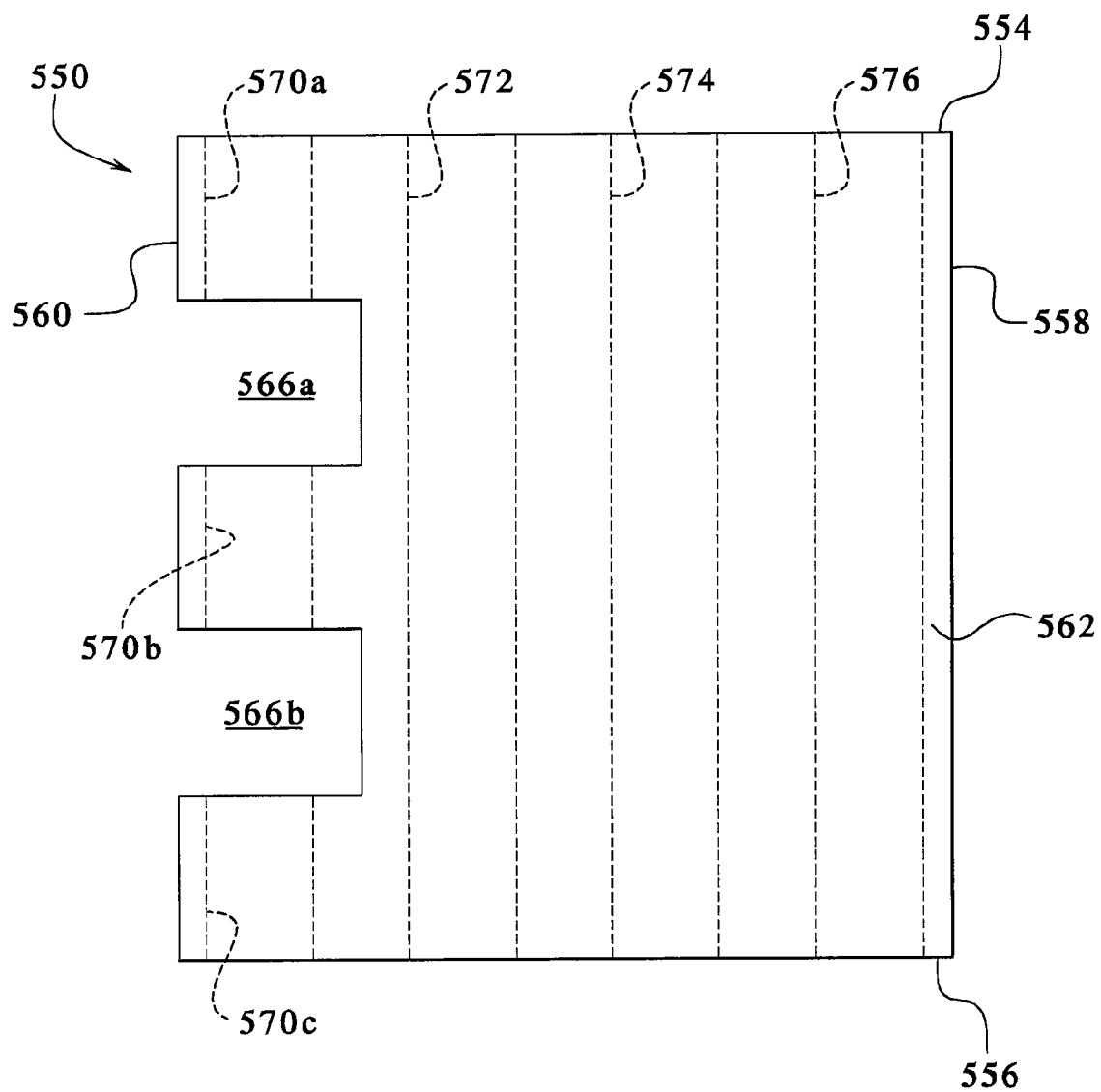
FIG. 14 is a side view of an elongated probe holder of a further alternative embodiment.

In a further embodiment, illustrated in FIG. 14, the probe holder 550 is elongated, enabling it to be simultaneously positioned adjacent to both biopsy needle holders or arms. The probe holder is formed as one body and thus performs the same function as the separate probe holders described above. In one such embodiment, the two probe holders are integrally formed. The body of the probe holder 550 includes a top wall or surface 554, a bottom wall or surfaces 556, a front wall or surface 558, a rear wall or surface 560, and two side walls or surfaces 562 and 564 (not shown). The rear or first portion or section of the body includes or defines needle holder arm receiving areas 566a and 566b each sized and configured to receive the end section of the respective biopsy needle holder arms. The rear or first portion or section of the body also defines or includes vertically aligned laser probe receiving channels 570a, 570b and 570c. The probe holder 550 also includes a front or second portion or section defining spaced-apart parallel or substantially parallel thermal probe receiving channels 572, 574, and 576 extending from the top wall or surface 554 to the bottom wall or surface 556. This embodiment can be used in certain situations where the distance between the biopsy needle holder arms is fixed. Alternatively, a set of these probe holders 550 may be provided such that each probe holder has a different distance between arm receiving areas 566a and 566b.

Figure 15:
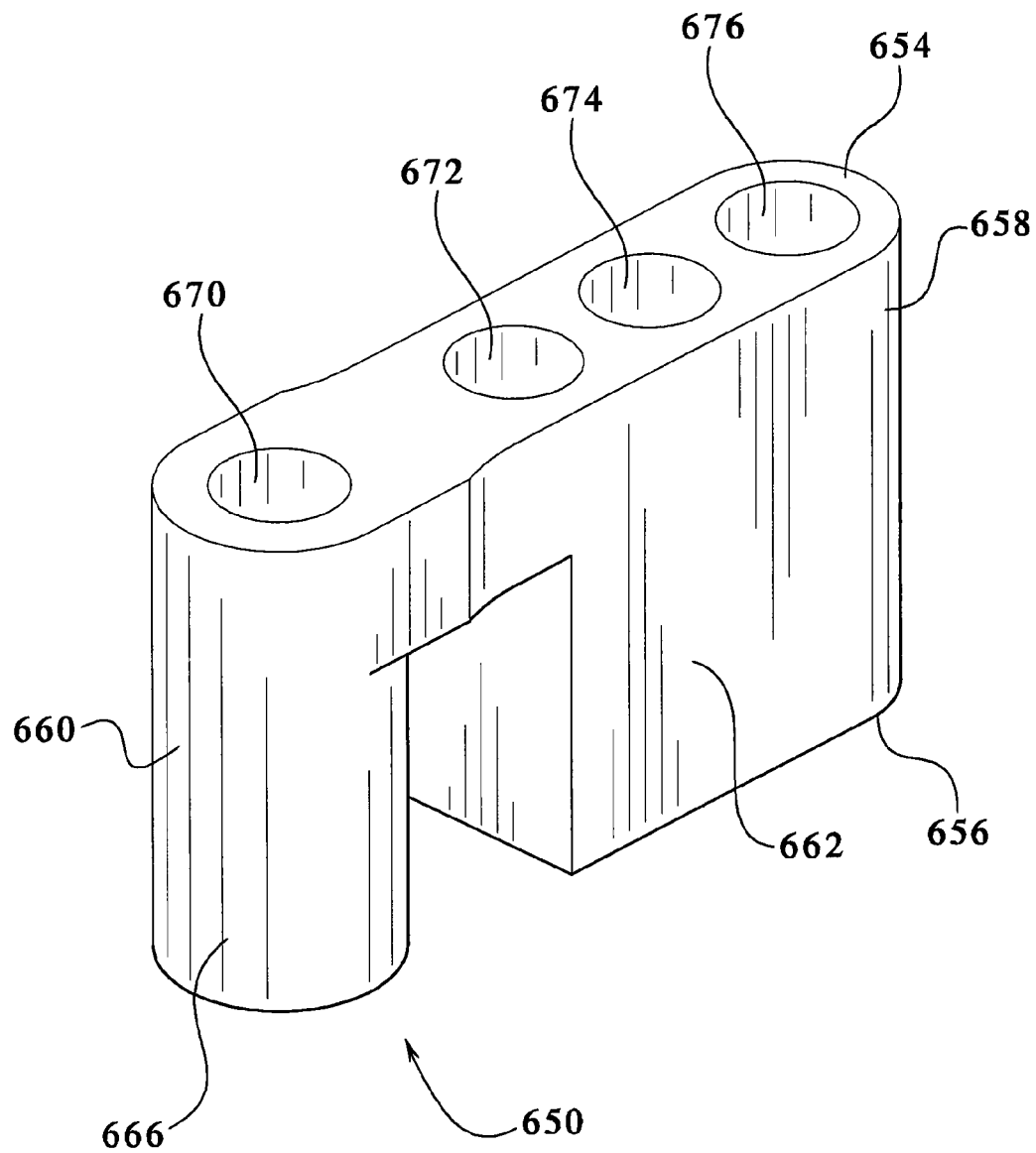
FIG. 15 is a top perspective view of a further embodiment of the probe holder.
Figure 16:
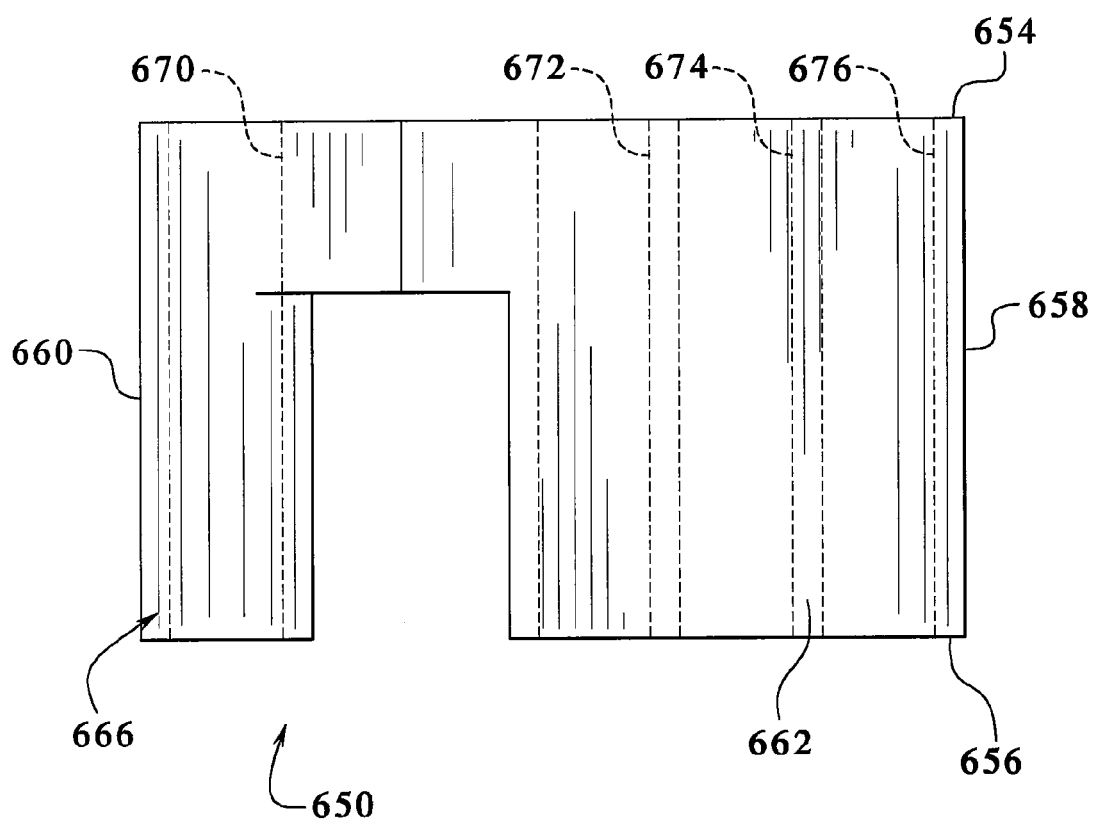
FIG. 16 is a side view of the embodiment of the probe holder of FIG. 15.
Figure 17:
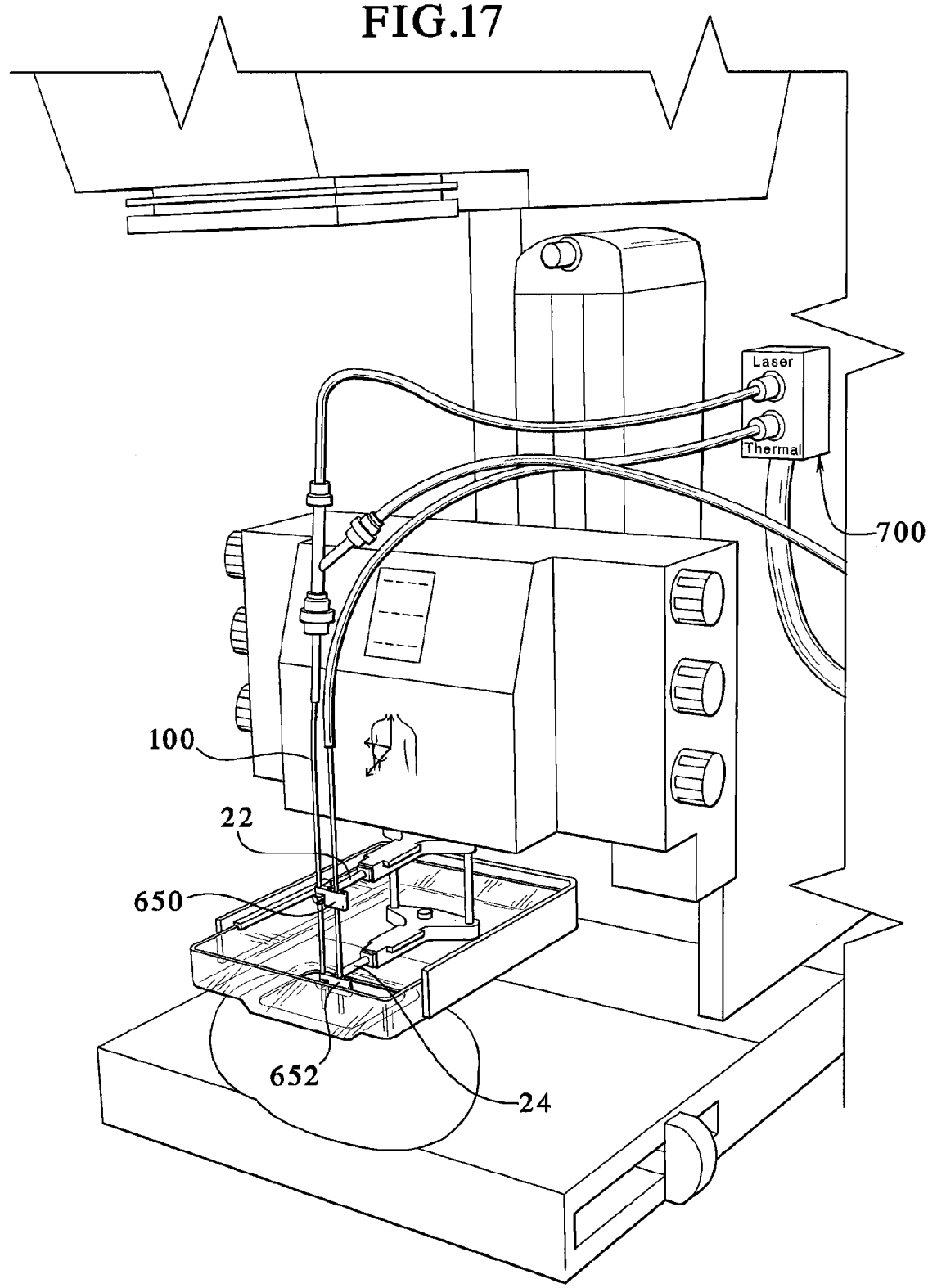
FIG. 17 is a fragmentary perspective view of another embodiment of the interstitial laser energy treatment apparatus disclosed herein, illustrating the laser probe holders of FIGS. 15 and 16 respectively aligned in first positions for positioning the laser probe and thermal probe in a first plane relative to tissue.

In a further embodiment, illustrated in FIGS. 15, 16, and 17, the probe holder 650 includes a body having a top wall or surface 654, a bottom wall or surface 656, a front wall or surface 658, a rear wall or surface 660, and two side walls or surfaces 662 and 664 (not shown). The rear or first portion or section of the body includes or defines an integrated bushing 666 for rotatably connecting the probe holder 650 to the biopsy needle holder arm. The integrated bushing 666 for rotatably connecting the probe holder 650 to the biopsy needle holder arm is positioned in the aperture of the arm 22. The rear or first portion or section of the body also includes or defines a vertically aligned laser probe receiving channel 670. The front or second portion or section of the body includes or defines vertically aligned thermal probe receiving channels 672, 674, and 676. It should be appreciated that in this embodiment, the probe holder 650 is maintained in position relative to the arm 22 by the integrated bushing 666 once inserted into the arm 22. Similarly, as illustrated in FIG. 17, the second probe holder 652 includes an integrated bushing 666 for rotatably connecting the probe holder 652 to the biopsy needle holder arm 24. It should be appreciated that the probe holders 650 and 652 are each pivotally movable with respect to the biopsy needle holder arms 22 and 24.

It should thus be appreciated that in operation, an operator positions both of the probe holders 650 and 652 in the arms 22 and 24 respectively, and then inserts the laser probe 100 through the laser probe channel 670 of probe holder 650, which is rotatably inserted in the aperture of the arm 22, and then through the laser probe channel 670 of probe holder 652. It should be appreciated that in this embodiment, the laser probes do not come in contact with the arms. This embodiment also more easily enables an operator to position the probe holders and then the probes.

It should also be appreciated that FIG. 17 illustrates a slightly modified connection box 700 for the laser probe and thermal probe. Specifically, FIG. 17 illustrates that both the laser fiber and the wire for transferring temperature data from the single thermistor on the laser are contained within a single cord enclosure. In this embodiment, the number of discrete cords or cables terminating at either of the two probes is thus reduced.

In one embodiment, the tissue (such as the tumor) is pierced with a laser probe to enable access to the tissue by a saline supply and a laser fiber for interstitial laser energy treatment. In one embodiment, the laser heats the tumor tissue using saline as a heat transfer medium. The thermal probe measures the temperature of the tissue adjacent to the tissue being treated.

More specifically, the illustrated embodiment of the interstitial laser treatment apparatus further includes a y-connector attached to the laser probe 100, which is configured to received a laser fiber and a saline supply tube. The laser fiber is connected to a suitable laser diode source such as one having 1-8 watts, 805 nominal nanometer wavelength. The saline supply tube is connected to a suitable syringe infusion pump (not shown) such as one capable of accurately dispensing 60 cc syringes of saline at variable flow rates to 1 cc per minute, continuously adjustable, and including bolus function. In one embodiment, the laser probe is a 14 gauge probe constructed of 304 stainless steel and has one thermistor attached. It should be appreciated that the number of thermistors may vary. In one embodiment, the thermal probe is a 14 gauge probe constructed of 304 stainless steel and has five thermistors attached. In one such embodiment, the thermistors are marked and referred to as T1, T2, T3, T4, and T5 (not shown).

In one embodiment, the interstitial laser treatment apparatus further includes a converter suitable to convert thermistor temperature to a digital signal. The laser probe is placed in the desired position with respect to the tissue to be treated (such as in the center of the tumor). In one embodiment, the laser probe contains the optical fiber, and thus guides laser energy, a temperature measuring device, and saline solution to the interior of the tissue (such as the tumor). The thermal probe is inserted in the probe holder such that it is positioned in the periphery of the tissue to be treated (such as the tumor). The thermal probe enables the operator to determine the tissue temperature at set distances from the tissue being treated and monitor the various temperatures.

Tissue temperature measurements are taken at various distances away from the tumor mass surface. This temperature data is utilized in conjunction with the relative distances of the temperature sensors to calculate the volume of tumor mass destroyed, and therefore is utilized to determine when the entire tumor mass is effectively destroyed, as discussed below. Enabling the operator to optimally position the thermal probe with respect to the laser probe is critical to enable the operator to monitor a concentric zone of heat emitted from the tip of the laser probe during treatment. The ability to monitor the concentric heat patterns of the laser probe is necessary to effectively measure the volume of tissue (such as the tumor) mass destroyed during treatment.

As previously discussed, the relative positioning of the thermal probe and the laser probe must be determined and known to accurately calculate the volume of tumor mass destroyed. The thermal probe and laser probe may include a number of position marks (not shown) to enable an operator determine the relative positions of the thermal probe and laser probe. The position marks are preferably evenly spaced-apart along a portion of a length of the thermal probe and along a portion of the length of the laser probe. The operator may use these position marks to correctly position the laser probe, and subsequently position the thermal probe relative to the laser probe, as each probe is inserted in one of the probe receiving channels in the probe holders.

It should also be appreciated that a conventional treatment platform (not shown) may be positioned relative to the imaging device or unit to enable the interstitial laser therapy to be performed while the patient (not shown) is lying on the treatment platform. The use of the treatment platform with the imaging unit enables the interstitial laser therapy to be performed and, if necessary, adjunctive therapy to be performed in the same treatment room without transferring the patient to a new platform as described in one of the patents mentioned above.

It should be appreciated that the present disclosure is not limited to interstitial last energy therapy, and particularly, interstitial laser energy therapy for the destruction of a breast tumor. The present disclosure may apply to a variety of different non-surgical treatments for the destruction of a variety of different tumor masses.

It should be understood that modifications and variations may be effected without departing from the scope of the novel concepts of the present disclosure, and it should be understood that this application is to be limited only by the scope of the appended claims.

The invention is claimed as follows:

1. An interstitial energy treatment probe holder comprising:
   a handheld body having:
   (a) a first section including a top-most surface and a bottom-most surface, said first section defining at least one energy probe receiving channel, the at least one energy probe receiving channel configured to engage an energy probe such that the energy probe extends substantially along a first axis through the at least one energy probe receiving channel, through and beyond the top-most surface of the first section, and through and beyond the bottom-most surface of the first section; and
   (b) a second section including a top-most surface and a bottom-most surface, said second section connected to the first section and defining at least one thermal probe receiving channel including a first thermal probe receiving channel at a first predetermined distance from the at least one energy probe receiving channel, the first thermal probe receiving channel configured to engage a thermal probe such that the thermal probe can extend substantially along a second axis through the first thermal probe receiving channel, through and beyond the top-most surface of the second section, and through and beyond the bottom-most surface of the second section, said second axis being different than said first axis,
   the handheld body configured to:
   (a) engage the energy probe in a user-selected position with respect to the thermal probe during an interstitial energy treatment; and
   (b) engage the thermal probe at the first predetermined distance from the energy probe during said interstitial energy treatment.

2. The interstitial energy treatment probe holder of claim 1, wherein the second section defines a plurality of thermal probe receiving channels.

3. The interstitial energy treatment probe holder of claim 1, wherein the first section defines a plurality of aligned energy probe receiving channels.

4. The interstitial energy treatment probe holder of claim 1, wherein the second section includes a second thermal probe receiving channel at a second predetermined distance from the at least one energy probe receiving channel, the second thermal probe receiving channel configured to engage the thermal probe such that the thermal probe can extend substantially along a third axis through the second thermal probe receiving channel, through and beyond the top-most surface of the second section, and through and beyond the bottom-most surface of the second section, said third axis being different than said first axis and different than said second axis, the second predetermined distance being greater than the first predetermined distance, the handheld body configured to hold the thermal probe at either the first predetermined distance from said energy probe or the second predetermined distance from said energy probe during said interstitial energy treatment.

5. An interstitial energy treatment probe holder comprising:
   a handheld body including:
   an energy probe section defining at least one energy probe receiving channel, the at least one energy probe receiving channel configured to engage an energy probe during an interstitial energy treatment such that the energy probe extends through the at least one energy probe receiving channel substantially along an energy probe axis during the interstitial energy treatment; and
   a thermal probe section connected to the energy probe section and defining at least one thermal probe receiving channel, the at least one thermal probe receiving channel configured to engage a thermal probe during the interstitial energy treatment such that the thermal probe extends through the at least one thermal probe receiving channel substantially along a thermal probe axis during the interstitial energy treatment, the thermal probe axis being a predetermined distance from the energy probe axis,
   the handheld body configured to:
   (a) engage the energy probe in a user-selected position during the interstitial energy treatment, and (b) engage the thermal probe at the predetermined distance from the energy probe during the interstitial energy treatment.

6. The interstitial energy treatment probe holder of claim 5, wherein the energy probe section includes a top-most surface and a bottom-most surface; the thermal probe section includes a top-most surface and a bottom-most surface; the at least one thermal probe receiving channel is configured to engage the thermal probe during the interstitial energy treatment such that the thermal probe extends through the at least one thermal probe receiving channel substantially along the thermal probe axis during the interstitial energy treatment, through and beyond the top-most surface of the thermal probe section, and through and beyond the bottom-most surface of the thermal probe section; and the at least one energy probe receiving channel is configured to engage the energy probe during the interstitial energy treatment such that the energy probe extends through the at least one energy probe receiving channel substantially along the energy probe axis during the interstitial energy treatment, through and beyond the top-most surface of the energy probe section, and through and beyond the bottom-most surface of the energy probe section.

7. The interstitial energy treatment probe holder of claim 6, wherein the top-most surface of the thermal probe section is co-planar with the top-most surface of the energy probe section and wherein the bottom-most surface of the thermal probe section is co-planar with the bottom-most surface of the energy probe section.

8. The interstitial energy treatment probe holder of claim 5, wherein the energy probe axis is a first energy probe axis, the thermal probe axis is a first thermal probe axis, and the predetermined distance is a first predetermined distance, and which further includes:
a second handheld body, the second handheld body including a second body energy probe section defining at least one second body energy probe receiving channel, the at least one second body energy probe receiving channel configured to engage the energy probe during the interstitial energy treatment such that the energy probe extends through the at least one second body energy probe receiving channel substantially along a second energy probe axis during the interstitial energy treatment, a second body thermal probe section connected to the second body energy probe section and defining at least one second body thermal probe receiving channel, the at least one second body thermal probe receiving channel configured to engage the thermal probe during the interstitial energy treatment such that the thermal probe extends through the at least one second body thermal probe receiving channel substantially along a second thermal probe axis during the interstitial energy treatment, the second thermal probe axis being a second predetermined distance from the second energy probe axis, the second predetermined distance being different than the first predetermined distance, the second handheld body configured to:
(a) engage the energy probe in the user-selected position during the interstitial energy treatment, and
(b) engage the thermal probe at the second predetermined distance from the energy probe during the interstitial energy treatment.

9. The interstitial energy treatment probe holder of claim 5, wherein the energy probe section defines a plurality of energy probe receiving channels.

10. The interstitial energy treatment probe holder of claim 5, wherein the thermal probe section defines a plurality of thermal probe receiving channels.

11. The interstitial energy treatment probe holder of claim 5, wherein the thermal probe section includes a plurality of spaced apart thermal probe receiving channels.

12. An interstitial energy treatment probe holder comprising:
a handheld body having a first section including a top-most surface and a bottom-most surface and a second section including a top-most surface and a bottom-most surface, said first section defining at least one energy probe receiving channel, the at least one energy probe receiving channel configured to engage an energy probe such that the energy probe extends substantially along a first axis through the at least one energy probe receiving channel, through and beyond the top-most surface of the first section, and through and beyond the bottom-most surface of the first section, and
said second section connected to the first section and defining at least one thermal probe receiving channel, the thermal probe receiving channel configured to engage a thermal probe such that the thermal probe extends substantially along a second axis through the at least one thermal probe receiving channel, through and beyond the top-most surface of the second section, and through and beyond the bottom-most surface of the second section, said second axis being different than said first axis, said second axis being a predetermined distance from the first axis, wherein the bottom-most surface of the first section and the bottom-most surface of the second section are in a same plane and wherein the top-most surface of the first section and the top-most surface of the second section are in different planes, the handheld body configured to:
(a) engage the energy probe in a user-selected position during an interstitial energy treatment, and
(b) engage the thermal probe at the predetermined distance from the energy probe during said interstitial energy treatment.

13. The interstitial energy treatment probe holder of claim 12, wherein the first section defines a plurality of energy probe receiving channels aligned along said first axis.

14. The interstitial energy treatment probe holder of claim 12, wherein the second section defines a plurality of thermal probe receiving channels aligned along said second axis.

15. The interstitial energy treatment probe holder of claim 12, wherein the second section defines a plurality of thermal probe receiving channels.

16. An interstitial energy treatment probe holder comprising:
a handheld body having:
(a) a first section including a top-most surface and a bottom-most surface, said first section defining at least one thermal probe receiving channel, the at least one thermal probe receiving channel configured to engage a thermal probe such that the thermal probe extends substantially along a first axis through the at least one thermal probe receiving channel, through and beyond the top-most surface of the first section, and through and beyond the bottom-most surface of the first section; and
(b) a second section including a top-most surface and a bottom-most surface, said second section connected to the first section and defining at least one energy probe receiving channel including a first energy probe receiving channel at a first predetermined distance from the thermal probe receiving channel, the first energy probe receiving channel configured to engage an energy probe such that the energy probe can extend substantially along a second axis through the first energy probe receiving channel, through and beyond the top-most surface of the second section, and through and beyond the bottom-most surface of the second section, said second axis being different than said first axis, the handheld body configured to:
(a) engage the thermal probe in a user-selected position with respect to the energy probe during an interstitial energy treatment; and
(b) engage the energy probe at the first predetermined distance from the thermal probe during said interstitial energy treatment.

17. The interstitial energy treatment probe holder of claim 16, wherein the second section defines a plurality of energy probe receiving channels.

18. The interstitial energy treatment probe holder of claim 16, wherein the first section defines a plurality of aligned thermal probe receiving channels.

19. An interstitial energy treatment probe holder comprising:
a handheld body including:
an thermal probe section defining at least one thermal probe receiving channel, the at least one thermal probe receiving channel configured to engage a thermal probe during an interstitial energy treatment such that the thermal probe extends through the at least one thermal probe receiving channel substantially along an thermal probe axis during the interstitial energy treatment; and
an energy probe section connected to the thermal probe section and defining at least one energy probe receiving channel, the at least one energy probe receiving channel configured to engage an energy probe during the interstitial energy treatment such that the energy probe extends through the at least one energy probe receiving channel substantially along an energy probe axis during the interstitial energy treatment, the energy probe axis being a predetermined distance from the thermal probe axis, the handheld body configured to:
(a) engage the thermal probe in a user selected position during the interstitial energy treatment when the thermal probe is in a patient, and
(b) engage the energy probe at the predetermined distance from the thermal probe during the interstitial energy treatment when the energy probe is also in the patient.

20. The interstitial energy treatment probe holder of claim 19, wherein the thermal probe section includes a top-most surface and a bottom-most surface; the energy probe section includes a top-most surface and a bottom-most surface; the at least one energy probe receiving channel is configured to engage the energy probe during the interstitial energy treatment such that the energy probe extends through the at least one energy probe receiving channel substantially along the energy probe axis during the interstitial energy treatment, through and beyond the top-most surface of the energy probe section, and through and beyond the bottom-most surface of the energy probe section; and the at least one thermal probe receiving channel is configured to engage the thermal probe during the interstitial energy treatment such that the thermal probe extends through the at least one thermal probe receiving channel substantially along the thermal probe axis during the interstitial energy treatment, through and beyond the top-most surface of the thermal probe section, and through and beyond the bottom-most surface of the thermal probe section.

21. The interstitial energy treatment probe holder of claim 20, wherein the top-most surface of the energy probe section is co-planar with the top-most surface of the thermal probe section and wherein the bottom-most surface of the energy probe section is co-planar with the bottom-most surface of the thermal probe section.

22. The interstitial energy treatment probe holder of claim 19, wherein the thermal probe section defines a plurality of thermal probe receiving channels.

23. The interstitial energy treatment probe holder of claim 19, wherein the energy probe section defines a plurality of energy probe receiving channels.

24. The interstitial energy treatment probe holder of claim 19, wherein the thermal probe section includes a plurality of spaced apart thermal probe receiving channels.

* * * * *

UNITED STATES PATENT AND TRADEMARK OFFICE
CERTIFICATE OF CORRECTION

| | | |
|---|---|---|
| PATENT NO. | : 8,926,677 B2 | Page 1 of 1 |
| APPLICATION NO. | : 13/967703 | |
| DATED | : January 6, 2015 | |
| INVENTOR(S) | : Anthony J. Tomasello et al. | |

It is certified that error appears in the above-identified patent and that said Letters Patent is hereby corrected as shown below:

IN THE CLAIMS

In Claim 19, Column 13, Line 24, replace "an" with --a--.
In Claim 19, Column 13, Line 30, replace "an" with --a--.

Signed and Sealed this
Twelfth Day of May, 2015

Michelle K. Lee
*Director of the United States Patent and Trademark Office*